United States Patent [19]

Shibatani et al.

[11] Patent Number: 5,846,811
[45] Date of Patent: Dec. 8, 1998

[54] GENE PARTICIPATING IN THE MECHANISM OF SECRETION OF ESTERASE

[75] Inventors: Takeji Shibatani, Kobe; Hiroyuki Akatsuka, Moriguchi; Eri Kawai, Kusatsu, all of Japan

[73] Assignee: Tanabe Seiyaku Co., Ltd., Osaka, Japan

[21] Appl. No.: 620,605

[22] Filed: Mar. 22, 1996

[30] Foreign Application Priority Data

Mar. 23, 1995 [JP] Japan .................................. 7-063772

[51] Int. Cl.$^6$ .............................. C12N 1/20; C12N 9/16; C07H 21/04; C12P 21/06
[52] U.S. Cl. ..................... 435/252.33; 536/23.1; 536/23.7; 435/69.1; 435/252.3; 435/320.1; 435/196; 435/880; 530/350
[58] Field of Search .............................. 435/252.1, 252.3, 435/252.33, 196, 880; 530/350; 536/23.2, 23.1, 23.7

[56] References Cited

U.S. PATENT DOCUMENTS 5,487,996   1/1996   Shibatani et al. ..................... 435/252.1

FOREIGN PATENT DOCUMENTS 0446771   9/1991   European Pat. Off. .
0544250   6/1993   European Pat. Off. .

Primary Examiner—Robert A. Wax
Assistant Examiner—Tekchand Saidha
Attorney, Agent, or Firm—Birch, Stewart, Kolasch & Birch, LLP

[57] ABSTRACT

A gene encoding a polypeptide which participates in the mechanism of secretion of esterase originated from a microorganism of the genus Serratia, a recombinant plasmid comprising a plasmid prepared by inserting said gene into a vector plasmid, a microorganism transformed with said recombinant plasmid, and a method for the production of an esterase which comprises cultivating the transformant microorganism as set forth above in a medium and collecting the produced esterase outside and inside the cells. Said transformed microorganism have remarkably excellent capability of extracellular secretion of esterase.

9 Claims, 1 Drawing Sheet

FIG 1

GENE PARTICIPATING IN THE MECHANISM OF SECRETION OF ESTERASE

FIELD OF INVENTION

This invention relates to a gene DNA coding for a polypeptide which participates in the mechanism of secretion of esterase by a microorganism of the genus Serratia, a recombinant plasmid containing said gene, a novel microorganism transformed with the recombinant plasmid, a novel microorganism containing simultaneously the above recombinant plasmid and a recombinant plasmid containing a gene coding for an esterase, and a process for producing an esterase by cultivating the novel microorganisms.

PRIOR ART

Recently, it has frequently been tried to utilize enzymes such as esterase in hydrolysis reaction. For such a purpose, there are known various esterases, for example, esterases originated from animals (e.g. pig liver, pig pancreas, etc.), and esterases produced by microorganisms, such as *Arthrobacter globiformis, Geotrichum candidum, Candida cylindracea, Pseudomonas fluorescens*, etc. Further, it is known that an esterase produced by *Serratia marcescens* is prepared by a recombinant DNA technology.

However, the known esterases or known methods for producing esterase have various problems. For instance, animal-origin esterases are very expensive, and these microorganisms-origin esterases had problems such that they were disadvantageous in activity, stability, or specificity, or that the esterase-producing microorganism had no high productivity. Moreover, even by using a gene recombinant microorganism, it is not necessarily easy to increase the esterase productivity thereof to the level applicable for industrial production merely by magnifying the esterase gene. Besides, even though the productivity of esterase is increased, the extracellular secretion of esterase is occasionally insufficient, and thereby complicated procedure is required for recovery of the enzyme.

As a result of various investigations, the present inventors have succeeded in obtaining a gene (DNA) coding for a polypeptide which participates in the mechanism of secretion of esterase by a microorganism of the genus Serratia and further have found that the esterase-producing microorganisms can show remarkably increased capability of secretion of esterase by transforming said microorganism with a recombinant plasmid containing said DNA. The present invention has been accomplished based on these new findings.

SUMMARY DESCRIPTION OF THE INVENTION

An object of the present invention is to provide a gene coding for a polypeptide which participates in the mechanism of secretion of esterase produced by a microorganism of the genus Serratia. Another object of the invention is to provide a recombinant plasmid prepared by inserting said gene into a vector plasmid and further a transformant containing said recombinant plasmid. A further object of the invention is to provide a method for the production of an esterase by cultivating said transformant and collecting the esterase accumulated outside and inside the cells of the transformant.

DETAILED DESCRIPTION OF THE INVENTION

The gene encoding a polypeptide which participates in the mechanism of secretion of esterase (hereinafter, referred to as "esterase secretory gene") is a double stranded DNA of 4466 base pairs having three open reading frames (ORF) within the sequence, specifically DNA having the nucleotide sequence shown in SEQ ID NO: 1 hereinafter.

The donor microorganisms for such an esterase secretory gene include any microorganisms belonging to the genus Serratia which has an esterase productivity, for example, *Serratia marcescens* Sr41 (FERM BP-487), *Serratia liquefaciens* ATCC 27592, *Serratia marcescens* ATCC 13880, *Serratia marcescens* ATCC 14764, *Serratia marcescens* ATCC 19180, *Serratia marcescens* ATCC 21074, *Serratia marcescens* ATCC 27117, *Serratia marcescens* ATCC 21212, etc.

The vector plasmid into which the esterase secretory gene is inserted includes any plasmids being replicable in transformed cells. Among them, preferred example of said plasmid includes plasmids which have a copy number of 1 to several thousands and contain a resistant marker against antibiotics such as ampicillin, kanamycin, chloramphenicol, and further contain an appropriate promoter such as lac, tac, or trp. Moreover, the vector plasmids may further contain a plasmid-stabilizing gene such as par and parB.

These vector plasmids include, for example, pLG339 [Gene, Vol. 18, 332 (1982)], pBR322 [Gene, Vol. 2, 95 (1977)], pUC18 [Gene, Vol. 33, 103 (1985)], pUC19 [Gene, Vol. 33, 103 (1985)], pHSG298 [Gene, Vol. 61, 63 (1987)], pHSG299 [Gene, Vol. 61, 63 (1987)], and the like.

The above vector plasmids are commercially available or can be obtained from microbial cells containing these plasmids by a conventional method, for example, by "cleared lysate method" (cf. Yasuyuki Takagi, "Procedure for Experiment in Genetic Engineering", page 125, published by Kodansha, 1980), or by "alkaline lysis method" [cf. Maniatis et al., "Molecular Cloning", page 368, Cold Spring Harbor Laboratory, U.S.A. (1982)].

The host microorganisms (both for the recombination of plasmids and for the expression of the desired esterase), include any microorganisms which can be transformed with the recombinant plasmid and can replicate the plasmid therein, and can express the gene on the plasmid and can produce a functional protein. These host microorganisms include, for example, microorganisms belonging to the genus Serratia or the genus Escherichia, specifically *Serratia marcescens* Sr41 and various mutant strains derived therefrom, for example, *Serratia marcescens* M-1 (FERM BP-4068), *Serratia marcescens* TT392 [cf. Journal of Bacteriology, Vol. 161, 1 (1985)], or *Escherichia coli* K12 DH5 [cf. Maniatis et al., "Molecular Cloning", 2nd volume, A10, Cold Spring Harbor Laboratory, U.S.A. (1989)].

In addition, there may be used as the host microorganisms any other microorganisms containing a recombinant plasmid to which an esterase gene of the genus Serratia is inserted, for example, *Serratia marcescens* TA5025 (FERM BP-4067).

The chromosomal DNA containing the esterase secretory gene can easily be obtained from microorganisms containing said gene by a conventional method, for example, by treating the microbial cells with a lysozyme and further with a surfactant (e.g. sodium lauryl sulfate, sodium N-lauroyl sarcosinate, etc.), extracting the cells thus treated with an organic solvent (e.g. phenol, chloroform, diethyl ether, etc.) to remove proteins, and then precipitating the DNA with ethanol [cf. Journal of Molecular Biology, Vol. 3, 208 (1961), and Biochimica et Biophysica Acta, Vol. 72, 619 (1963)].

The recombinant plasmid comprising the chromosomal DNA containing an esterase secretory gene and the vector plasmid DNA can easily be prepared by a conventional method, for example, by cleaving the chromosomal DNA and the plasmid DNA with an appropriate restriction endonuclease (e.g. EcoRI, BamHI, HindIII, SalI, SacI, etc.) and then treating the resultant with DNA ligase (e.g. T4 DNA ligase, *E. coli* DNA ligase, etc.), if required, after treating the resultant with a terminal transferase or DNA polymerase, subjecting to said treatment with DNA ligase [cf. Methods in Enzymology, Vol. 68, 41 (1979), and Yasuyuki Takagi, "Procedure for Experiment in Genetic Engineering", page 135, published by Kodansha, 1980].

Selection of the desired recombinant plasmid containing the esterase secretory gene from a mixture of recombinant plasmids obtained by the above procedure can be done as follows.

Microbial cells being restriction endonuclease deficient and having esterase productivity, for example *Escherichia coli* K12 DH5 harboring a recombinant plasmid which contains an esterase gene (e.g. pLIPE111 disclosed in Japanese Patent First Publication (Kokai) No. 344891/1993, etc.) are transformed with the esterase-secretory gene-containing recombinant plasmids, and the thus-transformed cells are spread onto an agar medium containing an emulsified triglyceride in which the cell can grow, for example, a nutrient agar medium containing tributyrin emulsified with polyoxyethylene cetyl alcohol ether (Brij 58) and also containing a prescribed concentration of an antibiotic. After incubation at 30° to 37° C. for 1 to 2 days, the colony of a transformant around which a large clear zone is formed is isolated.

The above introduction of the recombinant plasmid into the host microorganism is carried out by a conventional method, for example, by treating the host cells with an aqueous calcium chloride solution at a low temperature to increase the membrane permeability of the cells and then introducing the recombinant plasmid into the host cells [cf. Journal of Molecular Biology, Vol. 53, 159 (1970)], or by an electroporation method.

The desired transformant may also be selected by the procedure comprising transforming cells of a microorganism (e.g. *Escherichia coli* K12 DH5, etc.) with a recombinant plasmid produced by inserting both of a DNA participating in the esterase secretory mechanism and of an esterase gene into a single vector plasmid, and then treating the resultant transformed cells in the same manner as described above.

Then, the plasmid DNA is extracted from the transformant by "alkaline lysis method" to give the recombinant plasmid, i.e. a plasmid produced by inserting an esterase gene of *Serratia marcescens* into a vector plasmid.

In order to make the transformation efficient, the recombinant plasmid thus obtained is modified in a microorganism which is restriction endonuclease deficient and is the same species of the host microorganism to be used for expressing the esterase. That is, when the host microorganism to be used is *Serratia marcescens* Sr41, the recombinant plasmid obtained above is introduced into *Serratia marcescens* TT392, which is restriction enzyme deficient strain. The recombinant plasmid thus modified is isolated from the microorganism. The modified recombinant plasmid is then introduced into a host microorganism to obtain the desired transformant suitable for the production of the desired esterase.

The introduction of the recombinant plasmid into the host microorganism can easily be done by the method of Takagi & Kizumi [cf. Journal of Bacteriology, Vol. 161, 1 (1985)], and the isolation of the plasmid can be done, for example, by alkaline lysis method. Besides, the desired transformant may be obtained by isolating the colony expressing antibiotics resistance. The host microorganisms to be used for said transformation include the above-mentioned microorganisms but are preferably strains having high esterase productivity.

The transformed microorganisms obtained by the above-mentioned method are, for example, *Serratia marcescens* TA5030 which is obtained by introducing a recombinant plasmid into *Serratia marcescens* Sr41 wherein said recombinant plasmid being obtained by inserting an about 2.6 kb SalI-BstPI DNA fragment containing an esterase gene and an about 6.5 kb EcoRV-EcoRV DNA fragment containing an esterase secretory gene into a vector plasmid pMW119; *Serratia marcescens* TBS90 which is obtained by introducing a recombinant plasmid into *Serratia marcescens* Sr41 wherein said recombinant plasmid being obtained by inserting an about 2.6 kb SalI-BstPI DNA fragment containing an esterase gene and an about 9.0 kb BamHI-SacI DNA fragment containing an esterase secretion gene into a vector plasmid pMW119. These transformed strains all have the same morphological characteristics as those of the host microorganism *Serratia marcescens* Sr41.

The production of esterase with the transformed microorganism obtained above is carried out by cultivating the microorganism in a medium and collecting the esterase outside and inside the cells of the microorganism.

The medium used for the production of esterase includes any conventional medium wherein the microorganism can grow. Suitable medium contains a carbon source such as saccharides (e.g. glucose, sucrose, molasses, etc.), organic acids (e.g. fumaric acid, citric acid, etc.), alcohols (e.g. glycerol, etc.), or amino acids (e.g. alanine, glutamine, asparagine, etc.) and a nitrogen source such as inorganic ammonium salts (e.g. ammonium sulfate, ammonium chloride, etc.), urea, peptone, corn steep liquor, yeast extract, casein hydrolysate, and the like. The carbon source is usually contained in an amount of 1 to 15 (W/V)% based on the medium, and the nitrogen source is usually contained in an amount of 0.1 to 2.0 (W/V)% based on the medium. The medium may optionally contain further an appropriate amount of an inorganic salt (e.g. phosphate, magnesium salt, potassium salt, calcium salt, etc.) and/or a metallic ion (e.g. iron, manganese, copper, zinc, etc.). In case of a synthetic medium, it may further contain vitamins or amino acids, and further, inducers for esterase production (e.g. vegetable oils, surfactants, etc.), defoaming agents, antibiotics which are suitable for stabilizing the recombinant plasmid in microorganisms. The medium is preferably adjusted to a pH 5 to 8.

The cultivation of the transformed microorganism is carried out by a conventional method. For example, the microorganism is inoculated into a medium and is cultivated by shaking culture, aeration culture, standing culture, continuous culture, or the like. The cultivation conditions may vary depending on the kinds of the medium and cultivation methods, but may be any conditions suitable for growth of the microorganism, usually at the initial pH 5–8, at 20° to 40° C., for 1 to 2 days.

The esterase produced outside and inside the cultivated cells is collected by a conventional method. For example, the esterase contained in the medium is collected by means of salting out with an inorganic salt, precipitation with an organic solvent, absorption or desorption with ion exchange resin and various column chromatography, gel filtration, use of protein-precipitating agent, or a combination of these methods. The esterase accumulated within the cells is obtained by firstly disrupting the cells by a physical method such as frictional disrupting device (Dyno Mill) or a chemical means such as treatment with lysozyme, and then collecting the esterase in the cell extract by the above-mentioned method.

The esterase secretory gene of this invention is not limited to those of the DNA sequences disclosed specifically in the present specification but includes any gene having a DNA sequence obtained by modifications in the sequence such as insertion, deletion or substitution. That is, the esterase secretory gene may artificially be modified directly in a test tube by using a synthetic mutated DNA primer designed on the basis of the DNA sequence of the gene encoding an esterase specifically disclosed herein, or by using a chemical mutating agent such as formic acid, hydrazine sulfite. Further, a mutant gene may be obtained by treating an esterase producing strain with NTG or UV.

EXAMPLES

The present invention is illustrated by the following Examples but should not be construed to be limited thereto.

In the Examples, the esterase activity was measured by a convenient method (using Lipase Kit S wherein the substrate being dimercaprol tributyrate, manufactured by Dainippon Pharmaceutical Co., Ltd., Japan). It may also be measured by another method comprising subjecting the product to enzymatic reaction in olive oil (as a substrate) at pH 8.0, 37° C. for 20 minutes, and then measuring the amount of formed fatty acid, wherein the unit of esterase activity is expressed as $\mu$mols of fatty acid formed per minute.

Besides, the medium used in Examples has the following formulation, wherein "%" is W/V% unless specified otherwise.

LB medium: 1.0% of Bactotryptone (manufactured by Difco), 0.5% of Bacto Yeast Extract (manufactured by Difco), and 0.5% of sodium chloride.

LBG plate medium: 1.0% of Bactotryptone (manufactured by Difco), 0.5% of Bacto Yeast Extract (manufactured by Difco), 0.5% sodium chloride, and 1.0% of Gellan Gum (manufactured by Wako Pure Chemical Industries, Ltd., Japan).

Tributyrin-containing LBG plate medium: LBG plate medium containing 0.5 v/v% of tributyrin, 0.5% of polyoxyethylene cetyl alcohol ether, and 0.005% of ampicillin.

Esterase producing medium: 1.0% of dextrin, 2.0% of meast, 0.2% of ammonium sulfate, 0.1% of potassium dihydrogen phosphate, 0.05% of magnesium sulfate heptahydrate, 0.01% of calcium chloride dihydrate, 0.001% of ferrous sulfate heptahydrate, 0.5% of Tween 80, and 0.1% of colorin.

Example 1
(1) Preparation of Chromosomal DNA Containing an Esterase Secretory Gene Serratia marcescens Sr41 (FERM BP-487) was subjected to aerobic shaking culture in LB medium (200 ml) at 30° C. overnight, and then the cells were collected by centrifugation. The cells were suspended in 0.9% aqueous sodium chloride solution (200 ml) once and then collected by centrifugation in order to wash them. The cells thus washed were suspended in an aqueous solution of 50 mM Tris-HCl-50 mM disodium ethylenediamine tetraacetate (pH 7.5, 200 ml) containing 200 mg of lysozyme, and the mixture was allowed to stand at room temperature for one hour.

To the mixture was added sodium lauryl sulfate in a concentration of 0.5%, and thereto was further added Protenase K, and the mixture was mildly shaken at 50° C. for 3 hours to lyse the cells. The mixture was extracted twice with an equal volume of phenol saturated with an aqueous solution of 10 mM Tris-HCl-1 mM disodium ethylenediamine tetraacetate (pH 8.0) (hereinafter, referred to as "TE"), and further extracted twice with a mixture of equal volume of TE-saturated phenol and chloroform, and then the resultant aqueous phase was subjected to precipitation with ethanol. The precipitate was dissolved in TE to prepare a TE solution containing 2.5 mg of the chromosomal DNA containing an esterase secretory gene.

(2) Preparation of a Recombinant Plasmid DNA

The chromosomal DNA prepared in the above (1) (20 $\mu$g) was completely digested with restriction endonuclease SacI, which was extracted twice with a mixture of equal volume of TE-saturated phenol and chloroform. To the mixture was added 0.5 volume of 7.5M ammonium acetate, and the DNA was recovered by precipitating with two times volume of ethanol.

A plasmid vector pMWE121 was prepared by inserting an about 2.6 kb genome DNA fragment (SalI-BstPI fragment) containing an esterase gene originated from Serratia marcescens Sr41 into a vector plasmid pMW119. DNA (0.5 $\mu$g) of said plasmid vector pMWE121, which was completely digested with the same restriction enzyme as above, was dephosphated by treating with alkaline phosphatase (manufactured by Takara Shuzo Co., Ltd., Japan, 0.4 unit) at 56° C. for one hour, and the resultant was extracted twice with a mixture of equal volume of TE-saturated phenol and chloroform, and thereto was added 0.5 volume of 7.5M ammonium acetate, and then the vector plasmid DNA was recovered by precipitating with two times volumes of ethanol. The dephosphated plasmid vector thus obtained was mixed with the chromosomal DNA obtained above (3 $\mu$g) and ligated with a DNA ligation kit (manufactured by Takara Shuzo Co., Ltd.) at 4° C. for 16 hours to give the recombinant plasmid DNA.

(3) Transformation with the Recombinant Plasmid and Preparation of Colony Bank with E. coli Host The cells of E. coli DH5 were treated by the method of Hanahan [cf. Journal of Molecular Biology, Vol. 166, 557 (1983)] and thereto was added the reaction mixture containing a plasmid DNA obtained in the above (2), by which the transformation was effected. The cells thus treated were spread onto LBG plate medium containing ampicillin (50 $\mu$g/ml), and they were incubated at 37° C. overnight to give the transformant (about 50,000 strains) containing recombinant plasmids inserted with fragments of the chromosomal DNA of Serratia marcescens Sr41.

(4) Isolation and Identification of a Transformant Strain Containing an Esterase Secretory Gene When an esterase producing strain is inoculated to a tributyrin-containing LBG plate medium, the esterase produced in the medium decomposes tributyrin to give fatty acids, by which the triglyceride emulsion around the colony is modified to form a circular clear zone around the colonies.

By utilizing this phenomenon, the screening of transformants was effected.

The transformants (about 50,000 strains) obtained in the above (3) were inoculated to a tributyrin-containing LBG plate medium, which was incubated at 37° C. overnight, by which one strain forming a clear zone was isolated from the DNA bank of SacI.

The formation of this clear zone will be owing to the increase of ability of extracellulor secretion of esterase by introducing the recombinant plasmid containing an esterase secretory gene, because when *Serratia marcescens* Sr41 was inoculated to a tributyrin-containing LBG plate medium and incubated at 37° C. overnight, the formation of a clear zone was observed, but when the untransformed *E. coli* DH5 and the *E. coli* DH5 carrying a plasmid vector pMWE121 were inoculated to a tributyrin-containing LBG plate medium and incubated at 37° C. overnight, no formation of a clear zone was observed.

Besides, the transformant being capable of formation of a clear zone was cultivated in a LB medium (60 ml) containing ampicillin (200 μg/ml) by aerobic shaking culture at 37° C. overnight, and the esterase activity of the supernatant of the culture mixture was measured by the convenient method. As a result, there was observed 34,800 units of esterase activity.

Moreover, the supernatant of the above culture mixture was subjected to an electrophoresis with SDS polyacrylamide gel, and the resultant was subjected to Western blotting analysis by using rabbit antiesterase antibody to an esterase produced by *Serratia marcescens*. As a result, the product showed a new band, which was not shown in the product from *E. coli* DH5 containing only vector plasmid, at the same position as that in the purified standard esterase obtained from the supernatant of the culture of *Serratia marcescens* Sr41.

Example 2

Analysis of Plasmid

A plasmid DNA was prepared from the cells of the transformant obtained in Example 1-(4) by a conventional method [cf. Maniatis et al., "Molecular Cloning", page 368, Cold Spring Harbor Laboratory, U.S.A. (1982)], cleaved with various restriction endonucleases and then subjected to an agarose gel electrophoresis. As a result, it was confirmed that this plasmid (hereinafter, referred to as "pKHE200") contained a SacI DNA fragment of about 20.0 kb in addition to about 2.6 kb SalI-BstPI DNA fragment containing an esterase gene originated from *Serratia marcescens*.

Figure 1:
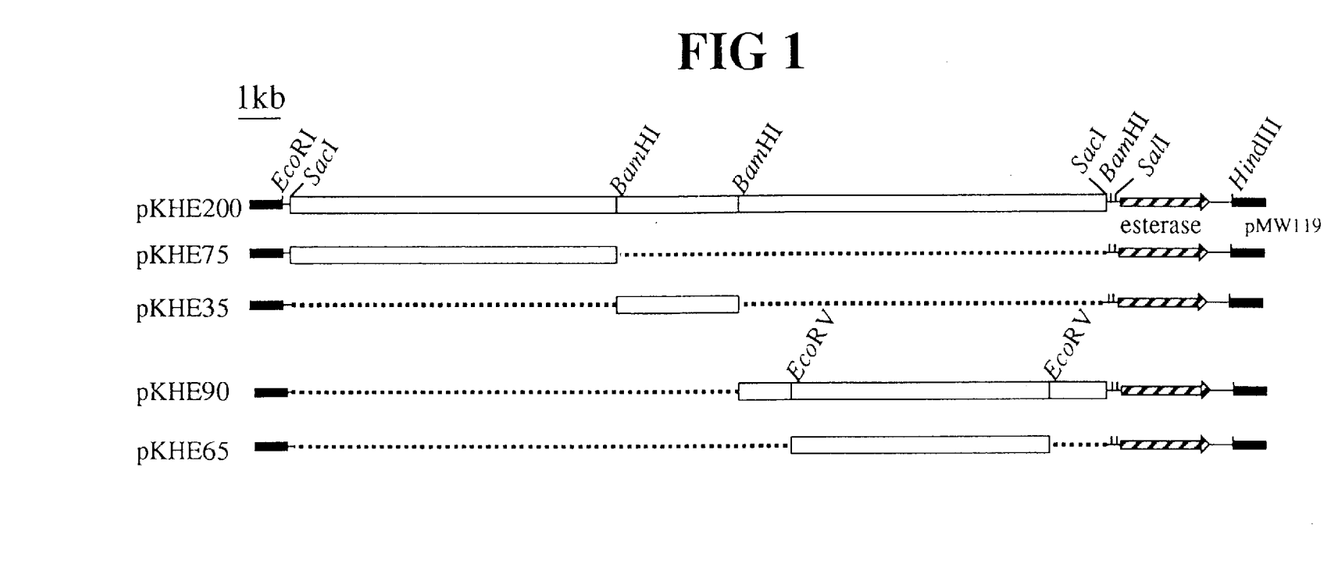
FIG. 1 shows restriction endonuclease maps of each of plasmid DNAs pPKHE200, pPKHE75, pPKHE35, pPKHE90 and pPKHE65 which were isolated from the recombinant cells in Example 2.

The restriction endonuclease map of the SacI DNA fragment of about 20.0 kb contained in said pKHE200 is shown in the accompanying FIG. 1.

The SacI DNA fragment of about 20.0 kb of the plasmid pKHE200 was cleaved with various restriction endonucleases, and each DNA fragment was subcloned into plasmid vector pMWE121, followed by transformation of *E. coli* DH5 with the recombinant plasmid thus obtained. The transformants were cultivated in a tributyrin-containing LBG plate medium in the same manner as described above, and it was determined whether a clear zone was formed or not.

The restriction endonuclease maps of each DNA fragment are shown in the accompanying FIG. 1. As to *E. coli* DH5 transformed with the plasmid containing BamHI-SacI DNA fragment of about 9.0 kb (pKHE90) and the plasmid containing EcoRV-EcoRV DNA fragment of about 6.5 kb (pKHE65), there were observed the formation of a clear zone and esterase activity (measured by the convenient method). However, as to *E. coli* DH5 transformed with the plasmid containing SacI-BamHI DNA fragment of about 7.5 kb (pKHE75) and with the plasmid containing BamHI-BamHI DNA fragment of about 3.5 kb (pKHE35), there was observed neither the formation of a clear zone nor esterase activity (measured by the convenient method).

It was found from the above results that the esterase secretory gene originated from *Serratia marcescens* Sr41 was present in the EcoRV-EcoRV DNA fragment of about 6.5 kb.

The *E. coli* DH5 transformed with the plasmid pKHE65 has been deposited to National Institute of Bioscience and Human-Technology, Agency of Industrial Science and Technology on Feb. 9, 1996 as accession number FERM BP-5385 (designated "*Escherichia coli* TA5029").

Example 3

Analysis of Clone DNA

[Determination of nucleotide sequence]

The recombinant plasmid pKHE65 was treated with Kilobase Deletion Kit (manufactured by Takara Shuzo Co., Ltd.) to prepare various deletion plasmids. These plasmids thus obtained were subjected to annealing of a primer, synthesis of complementary chain with Klenow fragment of DNA polymerase [labelled with ($\alpha$-$^{32}$P)dCTP (14.8×10$^6$ Bq/pmol, 74×10$^4$ Bq)] according to the dideoxy chain termination method of Sanger et al. [Proc. Natl. Acad. Sci. USA, Vol. 74, 5463 (1977)], and the nucleotide sequences thereof were determined based on the data of an electrophoresis with an 8% urea-modified poly-acrylamide gel and autoradiography.

As a result, it has been found that the DNA sequence of the esterase secretory gene originated from *Serratia marcescens* Sr41 is composed of 4466 base pairs from the initiation codon GTG to the codon GAG as shown in SEQ ID NO: 1, which contains DNA regions (ORF) coding for three kinds of polypeptides which participate in the mechanism of secretion of esterase. (It is assumed that these three ORFs compose a pair of operon.)

Besides, the amino acid sequences of the polypeptides coded by each ORF are shown in SEQ ID NO: 2, 3 and 4, respectively.

Example 4

Preparation of a Strain Having High Esterase Productivity

The plasmid pKHE65 was introduced into a restriction endonuclease-deficient strain, *Serratia marcescens* TT392, to give a transformed strain. The pKHE65 plasmid DNA modified with *Serratia marcescens* was extracted from the cells of the transformed strain by "alkaline lysis method". Then, *Serratia marcescens* Sr41 cells were transformed with the plasmid DNA obtained above by electroporation method to give a transformant *Serratia marcescens* TA5030). The thus-obtained transformant (one platinum loop) was inoculated to an esterase-producing medium containing ampicillin (500 μg/ml) and subjected to reciprocating shaking culture (shaking amplitude 7 cm, 120 r.p.m.) at 30° C. for 20 hours. The culture broth was centrifuged to give a supernatant having an esterase activity of about 3.5×10$^5$ unit/ml (measured by the convenient method). This strain had about 10 times higher esterase productivity than the host strain *Serratia marcescens* Sr41 and further about 2 times higher esterase productivity than *Serratia marcescens* Sr41 containing recombinant plasmid pMWE121 (used as a vector plasmid).

Effects of the Invention

The microorganism transformed with a recombinant plasmid containing an esterase secretory gene of the present invention have remarkably excellent capability of extracellular secretion of esterase. Accordingly, when an esterase-producing microorganism harboring a recombinant plasmid which contains an esterase gene is further transformed with the recombinant plasmid which contains the esterase secretory gene of the present invention, there can be obtained a microorganism having excellent properties in both of esterase productivity and extracellulor secretion of esterase, and the cultivation of said transformant can give the desired esterase on an industrial scale.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 4465 base pairs
( B ) TYPE: nucleic acid
( C ) STRANDEDNESS: double
( D ) TOPOLOGY: linear ( i i ) MOLECULE TYPE: genomic DNA ( v i ) ORIGINAL SOURCE:
( B ) STRAIN: Serratia marcescens Sr41

( x i ) SEQUENCE DESCRIPTION: SEQ ID NO:1:

| | | | | | | |
|---|---|---|---|---|---|---|
| GTGAATCAAT | TTATCCGCG | CAACGAAATT | GCGGATGTTA | TACGTACACG | CAGCAAAGTC | 60 |
| TTCTGGACCG | TTGGTATATT | TACTGCGTTT | ATTAACCTGT | TAATGCTGGT | TCCTTCCATT | 120 |
| TATATGCTCC | AGGTTTACGA | CCGGGTGCTG | CCTTCGCGCA | ATGAAATCAC | GCTGTTAATG | 180 |
| CTGACGCTGA | TCATGCTGGG | CATGTTCGGC | ATGATGTCGC | TGTTGGAATA | CGTGCGCAGC | 240 |
| ATGGTGGTGA | TCCGCATCGG | CAGCCAGCTG | GATATGCGTC | TCAACACGCG | AGTCTATACC | 300 |
| GCGGCCTACG | AAGCGAATCT | GAAAAACGGT | TCGTCTGACG | CCGGTCAGAT | GCTGAGCGAT | 360 |
| TTGACCAATC | TGCGCCAATT | CCTCACCGGT | AGCGCGCTGT | TCGCCTTCTT | TGATGCGCCG | 420 |
| TGGTTTCCGA | TCTATCTGTT | GGTGATATTC | CTCTTTAACC | CTTGGTTGGG | CCTTTTCGCC | 480 |
| CTGGTCGGTG | CGCTGTTGCT | GATCGCATTG | GCGGTAATCA | ATGAAGTGGT | TTCGAAAAAG | 540 |
| CCGCTGGGAG | AAGCCAGCAA | GCTGTCGATC | ATGTCAGGTA | ATTTGGCCAG | CACCAATCTG | 600 |
| CGAAATGCCG | AAGTGATCGA | GGCTTTGGGG | ATGTTGCCTA | ACCTGAAACG | CCGGTGGTTC | 660 |
| GGTCTGCACC | AGCGGTTCTT | GAACAGCCAA | CGCATCGCCA | GCGAACGCGC | ATCGCGGGTC | 720 |
| ACGTCAATCA | CCAAGTTCGT | GCGTATGTCG | CTGCAGTCCT | TAGTGTTGGG | CCTGGGGGA | 780 |
| TGGTTGGCGA | TTGATGGGCA | CATCACGCCC | GGCATGATGA | TCGCCGGTTC | TATATTGATG | 840 |
| GGGCGAACGT | TGGCGCCGAT | CGAGCAGGTC | ATTAACGTTT | GGAAAAGCTA | TAGCGCGGCC | 900 |
| AAACTTTCTT | ATGGCCGCTT | GGTCAAGCTG | CTGGAAACGC | ATCCGCAGCG | TGGTACCGGC | 960 |
| ATGTCGCTGC | CGCGTCCGGA | AGGTGTGCTC | TCCGTAGAAG | GCGTGACCGC | CACGCCTCCG | 1020 |
| GGATCGAAAG | GGGATGCGGT | GCTGCATAAC | GTAAGTTTTG | CCATTCAACC | CGGCGATGTG | 1080 |
| CTGGGGATTA | TCGGTCCGAG | TGCGTCGGGC | AAATCAACAT | TGGCGCGCTT | ACTGGTCGGT | 1140 |
| ATTTGGCCTG | TGAGCGAAGG | GATAGTGCGG | TTGGATAATG | CCGACATCTA | CCAGTGGAAC | 1200 |
| AAAGACGAAC | TGGGGCCCTA | TATCGGCTAT | CTGCCGCAGG | ACATCGAGTT | GTTCGCCGGC | 1260 |
| ACTATCGCCG | AGAACATCGC | TCGCTTTAAC | GACATCGATT | CAGAGAAGT | GATTGAGGCT | 1320 |
| GCCAAGCTGG | CTGGTGTGCA | TGAACTGATC | CTGCGTTTCC | CTAACGGTTA | CGATTCGGTG | 1380 |
| ATCGGCAACG | GTGGTGCAGG | GTTGTCCGGC | GGGCAGAAGC | AACGTATCGG | CCTGGCGCGG | 1440 |
| GCATTGTATG | GCGATCCCGC | GTTGGTGGTG | TTGGATGAGC | CTAACTCCAA | CCTGGATGAT | 1500 |
| GCCGGCGAGA | AAGCGTTGAA | CCAGGCCATC | ATGTTCCTTA | AACAGCGTAA | TAAGACGGTG | 1560 |

```
GTCCTGATCA CTCACCGCAC CAATCTGCTG TCGATGACCA GCAAGCTGTT GCTGTTGGTT    1620
AACGGGAACG TCAATGCATT CGGCCCAACG CAGCAGGTGC TGCAGGCGTT GGCGAATGCG    1680
CAAAAGCGC  AGGTGCCTCC GCAGGCGGTG CGTGCGGTGA ACTCCGAGCC GGATGAAGGC    1740
GAAATCCCTA AAACTCAAAT TAATTAAGCC GTGAACTTGC CCGGCGGCGC TTTTGCGTCG    1800
CCGACAGTCA AAGGAGTTGG TATGTCTACG CATATTGGCG AGCCGCAAGA CTCGTATACT    1860
GAAGAGATCC CACAAGATGA ACGGCGGTTT ACCCGTATGG GGTGGCTGGT GGTCGGGATC    1920
GGTCTGTTCG GGTTTTTAGC CTGGGCGGCC TTTGCGCCGT TGGATAAAGG GGTGGCGTCG    1980
CCGGGATCGG TAACCGTTTC CGGCAACCGC AAAACGGTGC AGGCCCCGGC CAGCGGCATC    2040
ATTAAGAATA TTGCGGTCAG AGATGGCGAC AAAGTGAAAG CCGGTGAGGT GCTGGTGCAG    2100
CTCAGCCAGG TGCAGGCTCA AGCTCAGGTT GATTCGCTGC GGGATCAGTA CTACACCACG    2160
CTGGCGACAG AAGGGCGCTT GCTGGCAGAA CGCGATGGGT TGAGCATAGT GACTTTCTCA    2220
CCCATTTTGG ACGCGGTGAA AGATAAACCT CGCGTGGCAG AAATCATTGC ATTGCAAACG    2280
CAGCTGTTCG CCTCCCGCCG CCAAGCGCTG CAAAGTGAAA TCGACGGCTA TAAGCAGTCA    2340
ATGGACGGAA TCCGTTTCCA ATTAAAGGA  CTGCAGGATT CGCGCGGTAA CAAACAGATC    2400
CAGCTTTCCA GCCTGCGTGA GCAGATGAAC AGCATGAAGC AGTTGGCGGC GGACGGTTAC    2460
CTACCGCGTA ACCGTTACCT GGAAGTGCAG CGCCAGTTTG CCGAGGTAAA TAGCAGCATT    2520
GATGAAACGG TGGGGCGGAT TGGCCAATTG CAAAAGCAGT TGCTGGAATC ACAGCAACGC    2580
ATCGATCAGC GTTTCGCCGA CTACCAGCGC GAAGTCAGAA CGCAGCTGGC GCAAACTCAA    2640
ATGGACGCCA GCGAATTCCG CAACAAGCTG CAAATGGCCG ATTTCGATCT GGGCAACACC    2700
GCCATCACCT CACCGGTGGA CGGCACCGTG GTTGGATTGA ATATCTTCAC TCAGGGGGC    2760
GTCGTGGGAG CGGGTGACCA CCTGATGGAC GTTGTGCCCA GCCAGGCGAC TTTGGTGGTG    2820
GATTCTCGCC TCAAAGTCGA CCTGTTCGAT AAGGTGTACA ACGGGTTGCC GGTGGATCTG    2880
ATGTTTACCG CCTTCAACCA AAACAAAACC CCGAAAATTC CGGGAACCGT CACCTTGGTT    2940
TCCGCCGACC GCCTGGTCGA CAAAGCCAAT GGCGAACCTT ACTACCAGAT GCAGGTCACG    3000
GTCTCGCCGG AGGGCATGAA AATGCTCAGT GGCGAGGACA TCAAGCCGGG GATGCCGGTG    3060
GAGGTGTTCG TGAAAACGGG GTCGCGCTCG CTGTTGAGCT ATCTGTTTAA ACCTATTTTG    3120
GATCGCGCTC ATACTTCATT AACCGAGGAA TAATTTTGAT TCATTCAAAA CGACAGGCTG    3180
CCGGTCTGGT TATCGGCACC CTTTTGTTTG CGATGTCTGC GCCGGTTTAT TCGATAGGGA    3240
TTTTAGACGC ATATTCGCTG GCATTAGAAA AGGACCCGAC CTTTCGGGCG GCTATAAAAG    3300
AGAAAGAAGC GGGAGATGAA AACGAAAATA TCGGCAGGGC AGGGCTGCTG CCGAAGGTAT    3360
CGCTGAACTA CCAGAATTCG CCGCGCAACT GGCAAACTCA GAAGTACCCG CAAAGCGACT    3420
TTTTCGGCAA TGTTTCGGAG GTTACCCGGC GGCAGCAATA TCGCAGCTAT TCCAGTTCGA    3480
TCACCTTGAC GCAGCCGCTG TTCGATTATG AAGCTTACGC CAGGTACAAA GCCGGCGTGG    3540
CGCAGACCAT GATGTCGGAC GAGACGTATC GCGGTAAGTT GCTGGATTTG GCGGTGAGGG    3600
TGATTAACGC CTATGTCGAA GTGGCTTATT CCAAGGATCA AATCGCGTTG GCCGAAGCTC    3660
AAAAGGCGGC TTACAAGGAA CAGCTGACTT TGAACGATCG CCTGATGAGC GCCGGTGAAG    3720
GTACCATTAC CGACGTATCC GAAACTCAGG CGCGCTATAG CCTGGCTGAA GCACAGGTGA    3780
TAGAAGCGCG CGATGCACTG GATGCCGCAC AGCGTGAATT GGAAGTAATT ATCGGCATGC    3840
CGCTGAACCA ACTGGATGAA TTGCAGGTCT TGCGGCCGGG TAAATTCAAA GTGGCGCCGT    3900
TAATCCCGTC CAAGTTCGAA GAGTGGCAAA AGATCGCGTT GGAGAACAAC CCTGTATTGG    3960
```

```
CCGCCTCGCG  TCATGGCGTG  GATGCTGCTA  AGTATGATGT  CGAAAGGAAA  CGGGCTGGCT     4020

TTATGCCACA  GGTTCAGCTG  TATGCTTCGC  ATTCGGAAAA  CGACGCCAGC  AGCGACAACA     4080

CGGTTAACCA  GAAATACCGT  ACTGACAGCA  TTGGCGTGCA  GGTCAGCATG  CCTATTTATT     4140

CCGGTGGCGG  TGTTTCGGCA  TCGACCCGCC  AGGCAGCGGC  GCGTTACGGG  CAAGCGATGT     4200

ATGAAATGGA  TGCGCAAACG  GGCACCACGC  TCAACGATCT  GCGCAAACAG  TACAATTTGT     4260

GTATTAGCAG  CAGCGCTAAA  GTGGCGGCCT  ATGAACTGGC  GGTTCAATCG  GCGACGACCC     4320

AGGTGACGGC  GACCCGGCAA  AGCGTGCTGG  CTGGGCAACG  TGTCAACGTC  GATGTGCTCA     4380

ATGCCGAACA  GCAGCTCTAT  AGCGCACAGG  CGATTTTGGC  CTCTGCTAAA  TACACTTATA     4440

TCAAATCCTG  GATCACCCT  ATTGAG                                              4465
```

( 2 ) INFORMATION FOR SEQ ID NO:2:

( i ) SEQUENCE CHARACTERISTICS:
        ( A ) LENGTH: 588 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Val  Asn  Gln  Phe  Ile  Pro  Arg  Asn  Glu  Ile  Ala  Asp  Val  Ile  Arg  Thr
 1              5                        10                       15

Arg  Ser  Lys  Val  Phe  Trp  Thr  Val  Gly  Ile  Phe  Thr  Ala  Phe  Ile  Asn
               20                       25                       30

Leu  Leu  Met  Leu  Val  Pro  Ser  Ile  Tyr  Met  Leu  Gln  Val  Tyr  Asp  Arg
              35                        40                       45

Val  Leu  Pro  Ser  Arg  Asn  Glu  Ile  Thr  Leu  Leu  Met  Leu  Thr  Leu  Ile
          50                       55                       60

Met  Leu  Gly  Met  Phe  Gly  Met  Met  Ser  Leu  Leu  Glu  Tyr  Val  Arg  Ser
 65                      70                       75                       80

Met  Val  Val  Ile  Arg  Ile  Gly  Ser  Gln  Leu  Asp  Met  Arg  Leu  Asn  Thr
                    85                       90                       95

Arg  Val  Tyr  Thr  Ala  Ala  Tyr  Glu  Ala  Asn  Leu  Lys  Asn  Gly  Ser  Ser
               100                      105                      110

Asp  Ala  Gly  Gln  Met  Leu  Ser  Asp  Leu  Thr  Asn  Leu  Arg  Gln  Phe  Leu
               115                      120                      125

Thr  Gly  Ser  Ala  Leu  Phe  Ala  Phe  Phe  Asp  Ala  Pro  Tyr  Phe  Pro  Ile
          130                      135                      140

Tyr  Leu  Leu  Val  Ile  Phe  Leu  Phe  Asn  Pro  Trp  Leu  Gly  Leu  Phe  Ala
145                      150                      155                      160

Leu  Val  Gly  Ala  Leu  Leu  Leu  Ile  Ala  Leu  Ala  Val  Ile  Asn  Glu  Val
                    165                      170                      175

Val  Ser  Lys  Lys  Pro  Leu  Gly  Glu  Ala  Ser  Lys  Leu  Ser  Ile  Met  Ser
               180                      185                      190

Gly  Asn  Leu  Ala  Ser  Thr  Asn  Leu  Arg  Asn  Ala  Glu  Val  Ile  Glu  Ala
               195                      200                      205

Leu  Gly  Met  Leu  Pro  Asn  Leu  Lys  Arg  Arg  Trp  Phe  Gly  Leu  His  Gln
          210                      215                      220

Arg  Phe  Leu  Asn  Ser  Gln  Arg  Ile  Ala  Ser  Glu  Arg  Ala  Ser  Arg  Val
225                      230                      235                      240

Thr  Ser  Ile  Thr  Lys  Phe  Val  Arg  Met  Ser  Leu  Gln  Ser  Leu  Val  Leu
                    245                      250                      255

Gly  Leu  Gly  Gly  Trp  Leu  Ala  Ile  Asp  Gly  His  Ile  Thr  Pro  Gly  Met
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 260 |     |     |     | 265 |     |     |     | 270 |     |     |
| Met | Ile | Ala | Gly | Ser | Ile | Leu | Met | Gly | Arg | Thr | Leu | Ala | Pro | Ile | Glu |
|     |     | 275 |     |     |     |     | 280 |     |     |     | 285 |     |     |     |
| Gln | Val | Ile | Asn | Val | Trp | Lys | Ser | Tyr | Ser | Ala | Ala | Lys | Leu | Ser | Tyr |
|     | 290 |     |     |     |     | 295 |     |     |     |     | 300 |     |     |     |
| Gly | Arg | Leu | Val | Lys | Leu | Leu | Glu | Thr | His | Pro | Gln | Arg | Gly | Thr | Gly |
| 305 |     |     |     |     | 310 |     |     |     |     | 315 |     |     |     |     | 320 |
| Met | Ser | Leu | Pro | Arg | Pro | Glu | Gly | Val | Leu | Ser | Val | Gly | Val | Thr |
|     |     |     |     | 325 |     |     |     |     | 330 |     |     |     |     | 335 |
| Ala | Thr | Pro | Pro | Gly | Ser | Lys | Gly | Asp | Ala | Val | Leu | His | Asn | Val | Ser |
|     |     |     | 340 |     |     |     |     | 345 |     |     |     |     | 350 |     |     |
| Phe | Ala | Ile | Gln | Pro | Gly | Asp | Val | Leu | Gly | Ile | Ile | Gly | Pro | Ser | Ala |
|     |     | 355 |     |     |     |     | 360 |     |     |     |     | 365 |     |     |     |
| Ser | Gly | Lys | Ser | Thr | Leu | Ala | Arg | Leu | Leu | Val | Gly | Ile | Trp | Pro | Val |
|     | 370 |     |     |     |     | 375 |     |     |     |     | 380 |     |     |     |     |
| Ser | Glu | Gly | Ile | Val | Arg | Leu | Asp | Asn | Ala | Asp | Ile | Tyr | Gln | Trp | Asn |
| 385 |     |     |     |     | 390 |     |     |     |     | 395 |     |     |     |     | 400 |
| Lys | Asp | Glu | Leu | Gly | Pro | Tyr | Ile | Gly | Tyr | Leu | Pro | Gln | Asp | Ile | Glu |
|     |     |     |     | 405 |     |     |     |     | 410 |     |     |     |     | 415 |     |
| Leu | Phe | Ala | Gly | Thr | Ile | Ala | Glu | Asn | Ile | Ala | Arg | Phe | Asn | Asp | Ile |
|     |     |     | 420 |     |     |     |     | 425 |     |     |     |     | 430 |     |     |
| Asp | Ser | Glu | Lys | Val | Ile | Glu | Ala | Ala | Lys | Leu | Ala | Gly | Val | His | Glu |
|     |     | 435 |     |     |     |     | 440 |     |     |     |     | 445 |     |     |     |
| Leu | Ile | Leu | Arg | Phe | Pro | Asn | Gly | Tyr | Asp | Ser | Val | Ile | Gly | Asn | Gly |
|     | 450 |     |     |     |     | 455 |     |     |     |     | 460 |     |     |     |     |
| Gly | Ala | Gly | Leu | Ser | Gly | Gly | Gln | Lys | Gln | Arg | Ile | Gly | Leu | Ala | Arg |
| 465 |     |     |     |     | 470 |     |     |     |     | 475 |     |     |     |     | 480 |
| Ala | Leu | Tyr | Gly | Asp | Pro | Ala | Leu | Val | Val | Leu | Asp | Glu | Pro | Asn | Ser |
|     |     |     |     | 485 |     |     |     |     | 490 |     |     |     |     | 495 |     |
| Asn | Leu | Asp | Asp | Ala | Gly | Glu | Lys | Ala | Leu | Asn | Gln | Ala | Ile | Met | Phe |
|     |     |     | 500 |     |     |     |     | 505 |     |     |     |     | 510 |     |     |
| Leu | Lys | Gln | Arg | Asn | Lys | Thr | Val | Val | Leu | Ile | Thr | His | Arg | Thr | Asn |
|     |     | 515 |     |     |     |     | 520 |     |     |     |     | 525 |     |     |     |
| Leu | Leu | Ser | Met | Thr | Ser | Lys | Leu | Leu | Leu | Leu | Val | Asn | Gly | Asn | Val |
|     | 530 |     |     |     |     | 535 |     |     |     |     | 540 |     |     |     |     |
| Asn | Ala | Phe | Gly | Pro | Thr | Gln | Gln | Val | Leu | Gln | Ala | Leu | Ala | Asn | Ala |
| 545 |     |     |     |     | 550 |     |     |     |     | 555 |     |     |     |     | 560 |
| Gln | Lys | Ala | Gln | Val | Pro | Pro | Gln | Ala | Val | Arg | Ala | Val | Asn | Ser | Glu |
|     |     |     |     | 565 |     |     |     |     | 570 |     |     |     |     | 575 |     |
| Pro | Asp | Glu | Gly | Glu | Ile | Pro | Lys | Thr | Gln | Ile | Asn |     |     |     |     |
|     |     |     | 580 |     |     |     |     | 585 |     |     |     |     |     |     |     |

( 2 ) INFORMATION FOR SEQ ID NO:3:

( i ) SEQUENCE CHARACTERISTICS:
        ( A ) LENGTH: 443 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

|     |     |     |     |     |     |     |     |     |     |     |     |     |     |     |
| --- | --- | --- | --- | --- | --- | --- | --- | --- | --- | --- | --- | --- | --- | --- |
| Met | Ser | Thr | His | Ile | Gly | Glu | Pro | Gln | Asp | Ser | Tyr | Thr | Glu | Ile |
| 1   |     |     |     | 5   |     |     |     |     | 10  |     |     |     |     | 15  |
| Pro | Gln | Asp | Glu | Arg | Arg | Phe | Thr | Arg | Met | Gly | Trp | Leu | Val | Gly |
|     |     |     | 20  |     |     |     |     | 25  |     |     |     |     | 30  |     |

-continued

| | | | | | | | | | | | | |
|---|---|---|---|---|---|---|---|---|---|---|---|---|
| Ile | Gly | Leu 35 | Phe | Gly | Phe | Leu 40 | Ala | Trp | Ala | Ala 45 | Phe | Ala | Pro | Leu | Asp |
| Lys 50 | Gly | Val | Ala | Ser | Pro 55 | Gly | Ser | Val | Thr | Val 60 | Ser | Gly | Asn | Arg | Lys |
| Thr 65 | Val | Gln | Ala | Pro 70 | Ala | Ser | Gly | Ile | Ile 75 | Lys | Asn | Ile | Ala | Val | Arg 80 |
| Asp | Gly | Asp | Lys | Val 85 | Lys | Ala | Gly | Glu | Val 90 | Leu | Val | Gln | Leu | Ser 95 | Gln |
| Val | Gln | Ala | Gln 100 | Ala | Gln | Val | Asp | Ser 105 | Leu | Arg | Asp | Gln | Tyr 110 | Tyr | Thr |
| Thr | Leu | Ala | Thr 115 | Glu | Gly | Arg | Leu 120 | Leu | Ala | Glu | Arg | Asp 125 | Gly | Leu | Ser |
| Ile | Val 130 | Thr | Pro | Ser | Phe | Ile 135 | Leu | Asp | Ala | Val | Lys 140 | Asp | Lys | Pro | Arg |
| Val 145 | Ala | Glu | Ile | Ile | Ala 150 | Leu | Gln | Thr | Gln | Leu 155 | Phe | Ala | Ser | Arg | Arg 160 |

| | | | | | | | | | | | | |
|---|---|---|---|---|---|---|---|---|---|---|---|---|
| Gln | Ala | Leu | Gln | Ser 165 | Glu | Ile | Asp | Gly | Tyr 170 | Lys | Gln | Ser | Met | Asp 175 | Gly |
| Ile | Arg | Phe | Gln 180 | Leu | Lys | Gly | Leu | Gln 185 | Asp | Ser | Arg | Gly | Asn 190 | Lys | Gln |
| Ile | Gln | Leu | Ser 195 | Ser | Leu | Arg | Glu 200 | Gln | Met | Asn | Ser | Met 205 | Lys | Gln | Leu |
| Ala | Ala 210 | Asp | Gly | Tyr | Leu | Pro 215 | Arg | Asn | Arg | Tyr | Leu 220 | Glu | Val | Gln | Arg |
| Gln 225 | Phe | Ala | Glu | Val | Asn 230 | Ser | Ser | Ile | Asp | Glu 235 | Thr | Val | Gly | Arg | Ile 240 |
| Gly | Gln | Leu | Gln | Lys 245 | Gln | Leu | Leu | Glu | Ser 250 | Gln | Gln | Arg | Ile | Asp 255 | Gln |
| Arg | Phe | Ala | Asp 260 | Tyr | Gln | Arg | Glu | Val 265 | Arg | Thr | Gln | Leu | Ala 270 | Gln | Thr |
| Gln | Met | Asp 275 | Ala | Ser | Glu | Phe | Arg 280 | Asn | Lys | Leu | Gln | Met 285 | Ala | Asp | Phe |
| Asp | Leu 290 | Gly | Asn | Thr | Ala | Ile 295 | Thr | Ser | Pro | Val | Asp 300 | Gly | Thr | Val | Val |
| Gly | Leu | Asn | Ile | Phe | Thr 310 | Gln | Gly | Gly | Val | Val 315 | Gly | Ala | Gly | Asp | His 320 |
| 305 | | | | | | | | | | | | | | | |
| Leu | Met | Asp | Val | Val 325 | Pro | Ser | Gln | Ala | Thr 330 | Leu | Val | Val | Asp | Ser 335 | Arg |
| Leu | Lys | Val | Asp 340 | Leu | Phe | Asp | Lys | Val 345 | Tyr | Asn | Gly | Leu | Pro 350 | Val | Asp |
| Leu | Met | Phe 355 | Thr | Ala | Phe | Asn | Gln 360 | Asn | Lys | Thr | Pro | Lys 365 | Ile | Pro | Gly |
| Thr | Val 370 | Thr | Leu | Val | Ser | Ala 375 | Asp | Arg | Leu | Val | Asp 380 | Lys | Ala | Asn | Gly |
| Glu 385 | Pro | Tyr | Tyr | Gln | Met 390 | Gln | Val | Thr | Val | Ser 395 | Pro | Glu | Gly | Met | Lys 400 |
| Met | Leu | Ser | Gly | Glu 405 | Asp | Ile | Lys | Pro | Gly 410 | Met | Pro | Val | Glu | Val 415 | Phe |
| Val | Lys | Thr | Gly 420 | Ser | Arg | Ser | Leu | Leu 425 | Ser | Tyr | Leu | Phe | Lys 430 | Pro | Ile |
| Leu | Asp | Arg 435 | Ala | His | Thr | Ser | Leu 440 | Thr | Glu | Glu | | | | | |

( 2 ) INFORMATION FOR SEQ ID NO:4:

( i ) SEQUENCE CHARACTERISTICS:
        ( A ) LENGTH: 437 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
Leu Ile His Ser Lys Arg Gln Ala Ala Gly Leu Val Ile Gly Thr Leu
 1               5                  10                  15

Leu Phe Ala Met Ser Ala Pro Val Tyr Ser Ile Gly Ile Leu Asp Ala
            20                  25                  30

Tyr Ser Leu Ala Leu Glu Lys Asp Pro Thr Phe Arg Ala Ala Ile Lys
        35                  40                  45

Glu Lys Glu Ala Gly Asp Glu Asn Glu Asn Ile Gly Arg Ala Gly Leu
    50                  55                  60

Leu Pro Lys Val Ser Leu Asn Tyr Gln Asn Ser Pro Arg Asn Trp Gln
65                  70                  75                  80

Thr Gln Lys Tyr Pro Gln Ser Asp Phe Phe Gly Asn Val Ser Glu Val
                85                  90                  95

Thr Arg Arg Gln Gln Tyr Arg Ser Tyr Ser Ser Ile Thr Leu Thr
                100                 105                 110

Gln Pro Leu Phe Asp Tyr Glu Ala Tyr Ala Arg Tyr Lys Ala Gly Val
            115                 120                 125

Ala Gln Thr Met Met Ser Asp Glu Thr Tyr Arg Gly Lys Leu Leu Asp
    130                 135                 140

Leu Ala Val Arg Val Ile Asn Ala Tyr Val Glu Val Ala Tyr Ser Lys
145                 150                 155                 160

Asp Gln Ile Ala Leu Ala Glu Ala Gln Lys Ala Ala Tyr Lys Glu Gln
                165                 170                 175

Leu Thr Leu Asn Asp Arg Leu Met Ser Ala Gly Glu Gly Thr Ile Thr
            180                 185                 190

Asp Val Ser Glu Thr Gln Ala Arg Tyr Ser Leu Ala Glu Ala Gln Val
    195                 200                 205

Ile Glu Ala Arg Asp Ala Leu Asp Ala Ala Gln Arg Gln Leu Glu Val
210                 215                 220

Ile Ile Gly Met Pro Leu Asn Gln Leu Asp Glu Leu Gln Val Leu Arg
225                 230                 235                 240

Pro Gly Lys Phe Lys Val Ala Pro Leu Ile Pro Ser Lys Phe Glu Glu
                245                 250                 255

Trp Gln Lys Ile Ala Leu Glu Asn Asn Pro Val Leu Ala Ala Ser Arg
            260                 265                 270

His Gly Val Asp Ala Ala Lys Tyr Asp Val Glu Arg Lys Arg Ala Gly
    275                 280                 285

Phe Met Pro Gln Val Gln Leu Tyr Ala Ser His Ser Glu Asn Asp Ala
290                 295                 300

Ser Ser Asp Asn Thr Val Asn Gln Lys Tyr Arg Thr Asp Ser Ile Gly
305                 310                 315                 320

Val Gln Val Ser Met Pro Ile Tyr Ser Gly Gly Gly Val Ser Ala Ser
                325                 330                 335

Thr Arg Gln Ala Ala Ala Arg Tyr Gly Gln Ala Met Tyr Glu Met Asp
            340                 345                 350

Ala Gln Thr Gly Thr Thr Leu Asn Asp Leu Arg Lys Gln Tyr Asn Leu
    355                 360                 365
```

```
Cys  I l e  S e r  S e r  S e r  A l a  L y s  V a l  A l a  A l a  T y r  G l u  L e u  A l a  V a l  G l n
     370                      375                    380

S e r  A l a  T h r  T h r  G l n  V a l  T h r  A l a  T h r  A r g  G l n  S e r  V a l  l e u  A l a  G l y
385                          390                        395                                   400

G l n  A r g  V a l  A s n  V a l  A s p  V a l  L e u  A s n  A l a  G l u  G l n  G l n  L e u  T y r  S e r
                    405                        410                            415

A l a  G l n  A l a  I l e  L e u  A l a  S e r  A l a  L y s  T y r  T h r  T y r  I l e  L y s  S e r  T r p
                    420                      425                              430

A s p  H i s  P r o  I l e  G l u
             435
```

What is claimed is:

1. An isolated esterase secretory gene encoding a polypeptide which is required for secretion of esterase originated from a microorganism of the genus Serratia.

2. The gene as claimed in claim 1 which has a DNA sequence as shown in SEQ ID NO: 1.

3. The gene as claimed in claim 1 which comprises a DNA encoding a polypeptide having an amino acid sequence as shown in SEQ ID NO: 2, NO: 3 or NO: 4.

4. A recombinant plasmid comprising a plasmid prepared by inserting the gene as set forth in claim 1 or claim 2 into a vector plasmid.

5. A microorganism transformed with the recombinant plasmid as set forth in claim 4.

6. A transformant microorganism which is obtained by transforming a host microorganism with a recombinant plasmid comprising a plasmid prepared by inserting a gene encoding an esterase originated from a microorganism of the genus Serratia and a gene encoding a polypeptide which secretion of esterase originated from a microorganism of the genus Serratia into a vector plasmid.

7. A transformant microorganism which is obtained by transforming a host microorganism with a recombinant plasmid comprising a plasmid prepared by inserting a gene encoding an esterase originated from a microorganism of the genus Serratia into a vector plasmid and a recombinant plasmid comprising a plasmid prepared by inserting a gene encoding a polypeptide which is required for secretion of esterase originated from a microorganism of the genus Serratia into a vector plasmid.

8. The microorganism as claimed in claim 6 or claim 7, wherein the host microorganism is a microorganism of the genus Serratia or a microorganism of the genus Escherichia.

9. A method for production of an esterase, which comprises cultivating the transformant as set forth in claim 6 or claim 7 in a medium, and collecting the esterase accumulated inside the cells and in the medium.

* * * * *